(12) United States Patent
Lehman et al.

(10) Patent No.: US 6,503,237 B1
(45) Date of Patent: Jan. 7, 2003

(54) ABSORBENT GARMENT WITH SEAMLESS LEAK GUARDS

(75) Inventors: John Ray Lehman, Neenah, WI (US); James Edward Tomsovic, Shiocton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/290,414

(22) Filed: Apr. 13, 1999

(51) Int. Cl.⁷ .................................................. A61F 13/15
(52) U.S. Cl. ............................ 604/385.28; 604/385.29; 604/396
(58) Field of Search ..................... 604/385.01, 385.23, 604/385.24, 385.25, 385.26, 385.27, 385.28, 385.29, 385.04, 396, 394

(56) References Cited

U.S. PATENT DOCUMENTS

| | | | | |
|---|---|---|---|---|
| 3,860,003 A | * | 1/1975 | Buell | 604/385.25 |
| 4,500,316 A | * | 2/1985 | Damico | 604/389 |
| 4,636,207 A | | 1/1987 | Buell | |
| 4,704,115 A | * | 11/1987 | Buell | 604/385.26 |
| 4,725,473 A | * | 2/1988 | Van Gompel et al. | 428/156 |
| 4,808,176 A | | 2/1989 | Kielpikowski | 604/385.2 |
| 4,909,803 A | * | 3/1990 | Aziz et al. | |
| 4,940,464 A | * | 7/1990 | Van Gompel et al. | 604/396 |
| 5,032,120 A | * | 7/1991 | Freeland et al. | |
| 5,364,382 A | * | 11/1994 | Latimer et al. | |
| 5,454,803 A | * | 10/1995 | Sageser et al. | 604/358 |
| 5,601,545 A | * | 2/1997 | Glaug et al. | 604/385.2 |
| 5,601,547 A | * | 2/1997 | Kato et al. | |
| H1674 H | * | 8/1997 | Ames et al. | 604/389 |
| 5,735,838 A | * | 4/1998 | Ronnberg et al. | 604/385.25 |
| 5,853,405 A | * | 12/1998 | Suprise | |
| 6,004,306 A | * | 12/1999 | Robles et al. | |

FOREIGN PATENT DOCUMENTS

| | | | |
|---|---|---|---|
| WO | 97/12571 | 4/1997 | A61F/13/15 |
| WO | 98/14156 | 4/1998 | |
| WO | 98/29080 | 7/1998 | A61F/13/56 |

* cited by examiner

Primary Examiner—Aaron J. Lewis
Assistant Examiner—Jamisue A. Webb
(74) Attorney, Agent, or Firm—Pauley Petersen Kinne & Erickson

(57) ABSTRACT

An absorbent garment having a pant-like configuration is constructed using side leak guards which are seamless, and which exhibit improved performance. The seamless leak guards are provided by incorporating a substantially liquid-impermeable outer cover into the garment having lateral edges which extend substantially beyond the lateral edges of the absorbent layer. Elastic bands attached to the outer cover urge the edges upward during wear, and against the wearer's body, to prevent leakage of waste material. The portions of the outer cover which extend laterally beyond the absorbent layer serve as seamless leak guards.

21 Claims, 3 Drawing Sheets

ABSORBENT GARMENT WITH SEAMLESS LEAK GUARDS

FIELD OF THE INVENTION

This invention is directed to an absorbent garment, such as a training pant, swimsuit, diaper, incontinence garment or similar absorbent vehicle, which has a leak guard between the absorbent midsection and the edges of the garment. The leak guard is provided without separately attached side flaps, by extending the outer cover beyond the absorbent midsection and to the edges which contact the legs, and by incorporating elastic into the garment edges adjacent to the legs.

BACKGROUND OF THE INVENTION

Disposable absorbent garments having a pant-like configuration are used for child training pants, adult incontinence garments, swimsuits and the like. Referring to FIG. 1, a prior art pant-like absorbent garment 2 includes a waste containment section 4 and two side portions 6 and 8 defining a waist opening 10 and a pair of leg openings 12 and 14. The side panel 6 includes stretchable panels 18 and 20 joined together at seam 30. The side panel 8 includes stretchable panels 24 and 26 joined together at seam 33. Seams 30 and 33 extend longitudinally from the waist opening 10 to the leg openings 12 and 14 of the garment 2.

The waste containment section 4 includes multiple layers (not shown) including, for instance, a liquid-permeable inner layer, an absorbent core layer, and a liquid-impermeable outer cover layer 16 which faces away from the wearer. The waste containment section 4 also includes elasticized waist portions 22 on the front and back of the garment. The leg opening portions 12 and 14 also include elastic portions 46 which extend substantially around the portion of the leg openings defined by the waste containment section 4.

The disposable garment also includes leak guards in both leg openings, which help prevent lateral leakage of waste material through the leg openings. The leak guards have commonly been provided by elasticized flap portions 50 which are connected to the interior of the garment along the lower part of each leg opening. During use, the elasticized flap portions 50 fit snugly against the wearer and effectively block most spillage of waste material from the leg openings.

In the past, the flap portions 50 used for the leak guard have required a separate manufacturing step to attach the flap material to the garment. Generally, the flaps 50 have been joined via seams 52. During active use, some separation at the seams 52 can occur, resulting in failure of the flaps 50 to serve as effective leak guards. Providing a seam which is both leakproof and durable has been challenging, and has added to manufacturing costs.

SUMMARY OF THE INVENTION

The present invention is directed to a disposable pant-like absorbent garment similar to the one described above, and having leak guards, except that the side flaps and seams required to join them have been eliminated. Instead of using flaps, seamless leak guards are provided by extending the liquid-impermeable outer cover layer substantially beyond the absorbent layer on both sides, and to a higher location on the garment and on the wearer. The outer cover extensions on both sides are reinforced at their edges by elastic bands which pull the outer cover extensions upward and away from the absorbent layer, and against the wearer's body.

The lateral extensions of the outer cover material, combined with the upward pulling of the elastic bands, provide the garment with seamless leak guards not requiring separately attached flaps. The need and expense of attaching side flaps are thus eliminated. The problem of leakage at the seams joining the flaps to the garment, is also eliminated.

With the foregoing in mind, it is a feature and advantage of the invention to provide a disposable pant-like absorbent garment with effective leak guards at the leg openings, without attaching flaps.

It is also a feature and advantage of the invention to provide a disposable absorbent garment with improved leak guards, by eliminating flap seams.

DETAILED DESCRIPTION OF THE PRESENTLY PREFERRED EMBODIMENTS

Figure 1:
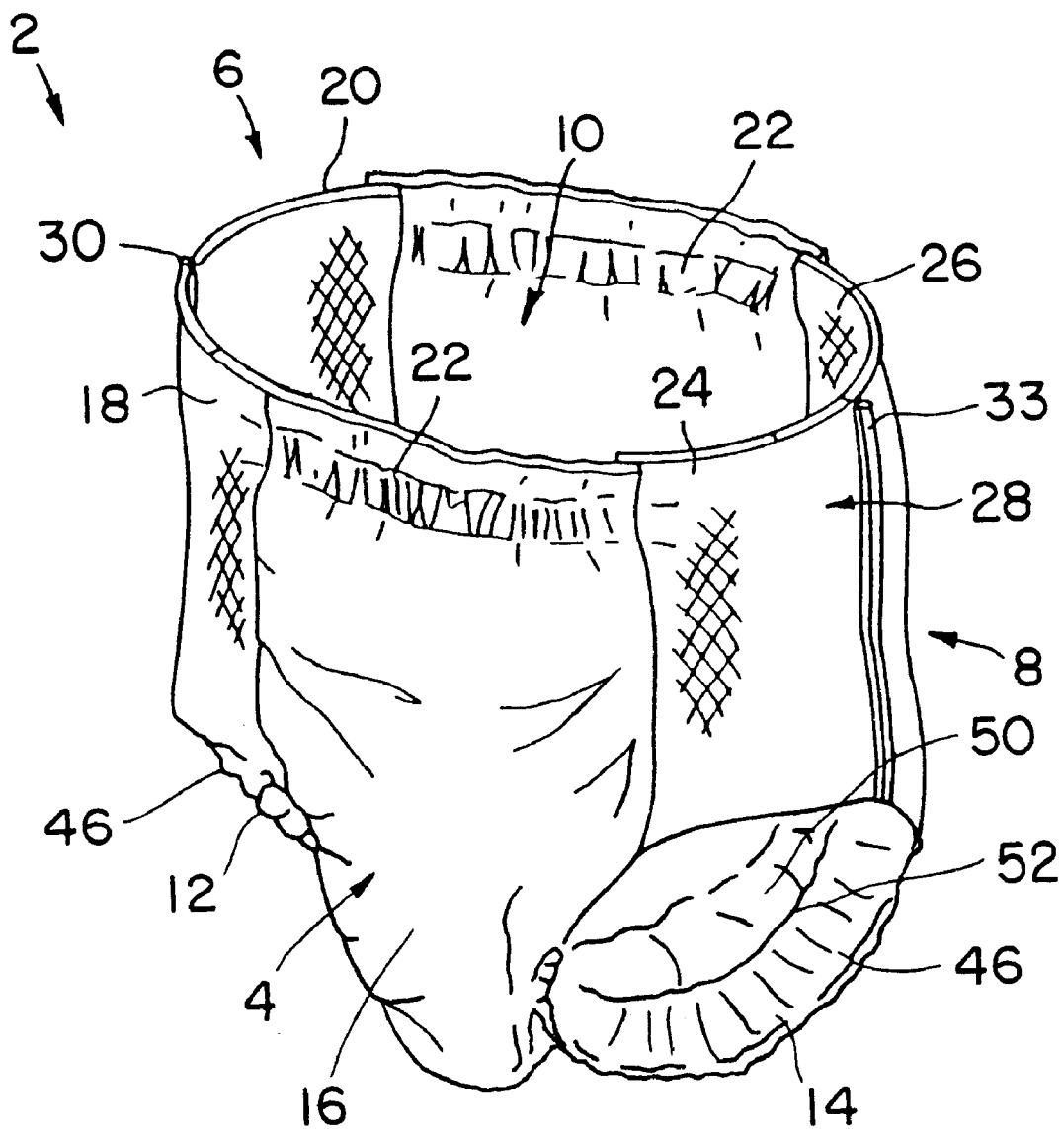
FIG. 1 (described above) is a perspective view of a prior art disposable absorbent garment, in which the leak guards are provided by attached flaps.
Figure 2:
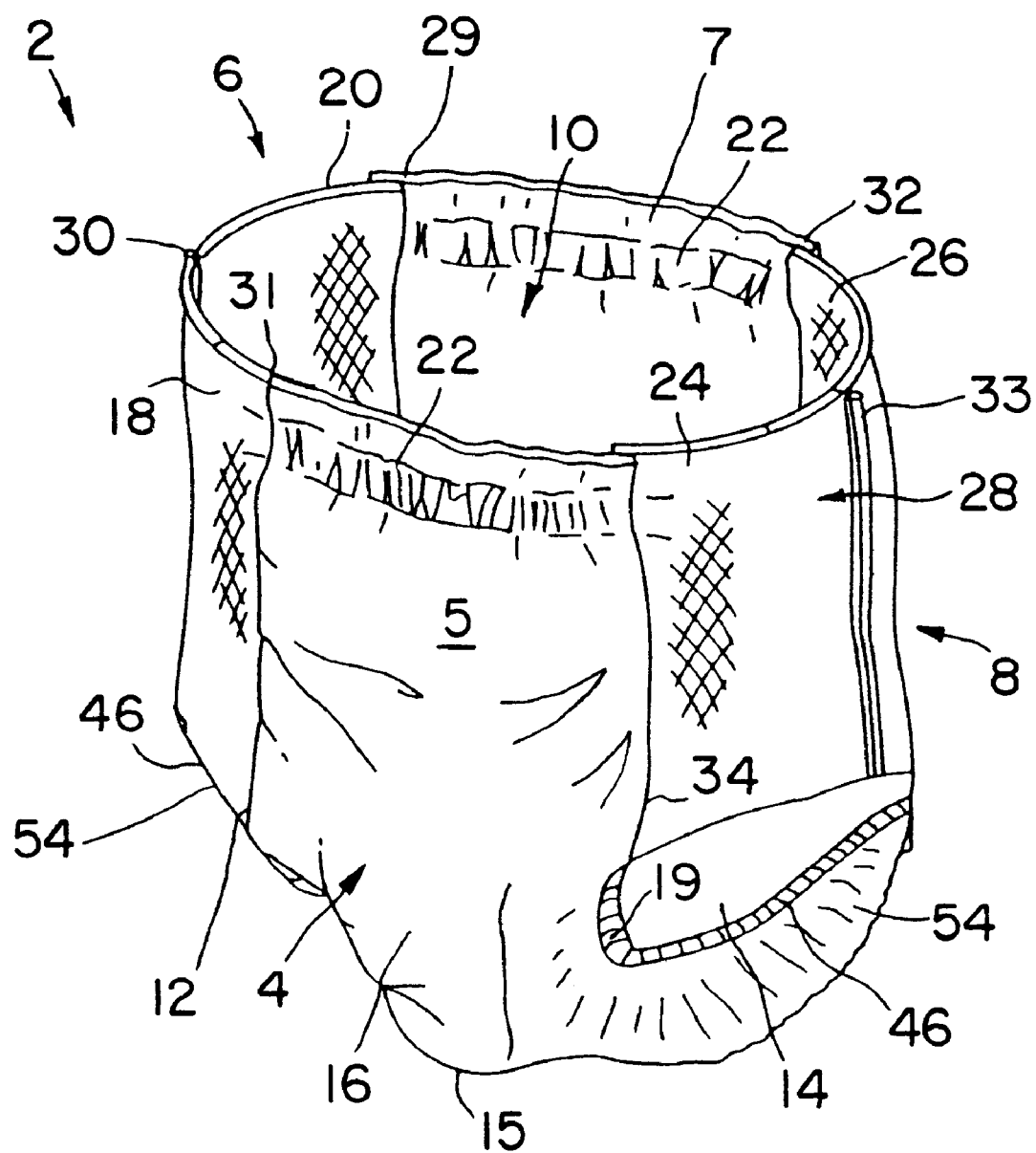
FIG. 2 is a perspective view of one embodiment of the flapless disposable absorbent garment of the invention.
Figure 3:
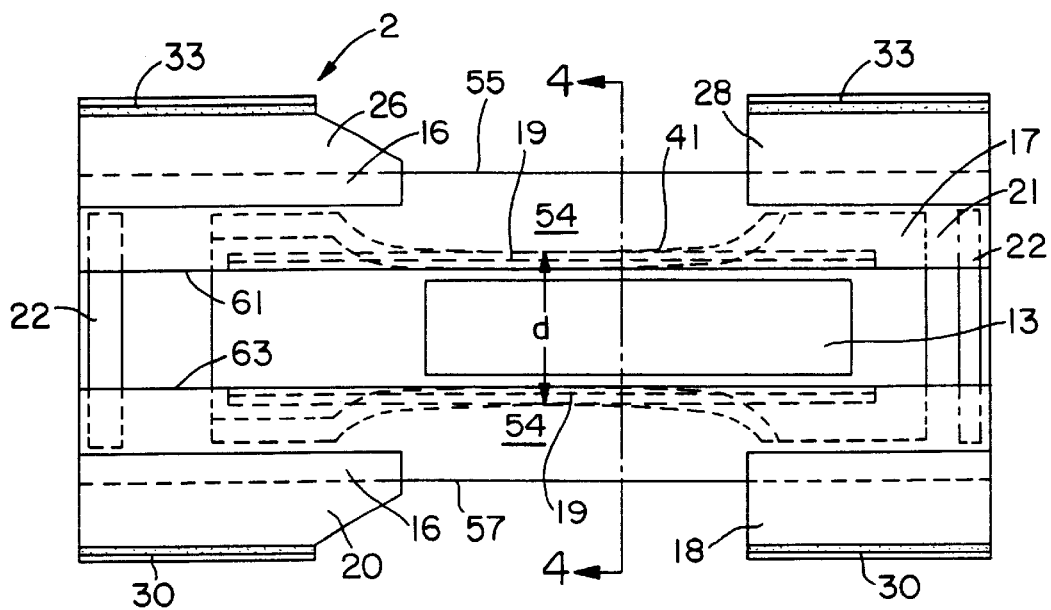
FIG. 3 is a plan view of the garment of FIG. 2, disconnected at the side seams, and laid out flat.
Figure 4:
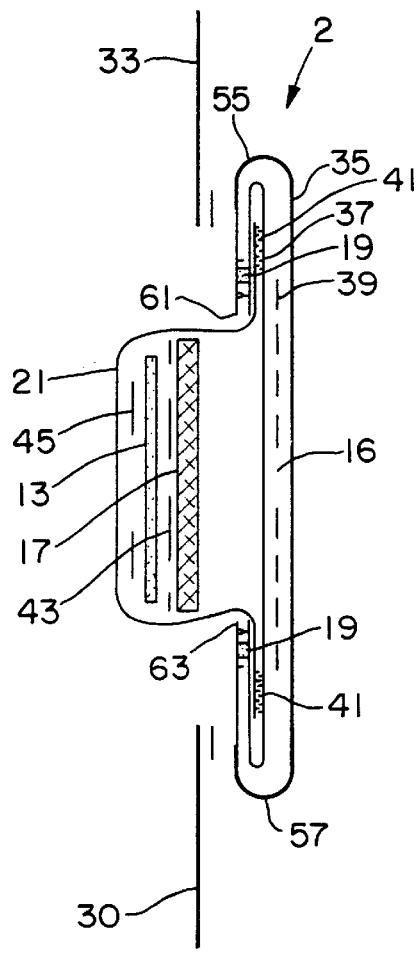
FIG. 4 is an expanded schematic sectional view of the garment of the invention taken along the lines 4—4 in FIG. 3 and showing each layer of the garment.

Referring to FIGS. 2–4 of the drawings, an absorbent garment 2 of the invention has a pant-like configuration useful for diapers, child training pants, child swimwear, adult incontinence articles, and the like. The garment 2 includes a waste containment section 4 having front portion 5 and rear portion 7 joined by central portion 15, and two side portions 6 and 8, each of which is connected at its edges to the front and rear portions. The side panel 6 includes stretchable panels 18 and 20 joined to each other along seam 30, and joined to the waste containment section along seams 29 and 31. Each of the seams 29, 30 and 31 is longitudinally oriented, and extends from the top of the waist opening 10 to the leg opening 12. The side panel 8 includes stretchable panels 24 and 26 joined to each other along seam 33, and joined to the waste containment section along seams 32 and 34. Each of the seams 32, 33 and 34 is longitudinally oriented, and extends from the top of the waist opening to the leg opening 14.

The longitudinal seams 29–34 may be formed by conventional methods including, without limitation, ultrasonic welding, thermal bonding, adhesive bonding, stitch bonding and the like. Ultrasonic welding is a presently preferred technique. The various bonding techniques are conventional, and are neither critical nor limiting as to the present invention.

The stretchable side panels 6 and 8 can be constructed of conventional woven or nonwoven materials, formed from a wide variety of elastic and stretchable polymers. The terms "elastic" and "stretchable" include any material which can be stretched, and which tends to return to its original shape when relaxed. Suitable polymers include without limitation block copolymers of polystyrene, polyisoprene and polybutadiene; copolymers of ethylene, natural rubbers and urethanes; and combinations of the foregoing. Particularly suitable are styrene-butadiene block copolymers sold by Shell Chemical Co. under the trade name KRATON®. Other suitable polymers include copolymers of ethylene, including without limitation ethylene vinyl acetate, ethylene methyl acrylate, ethylene ethyl acrylate, ethylene acrylic acid, stretchable ethylene-propylene copolymers, and combinations thereof. Also suitable are coextruded composites of the foregoing, and elastomeric staple integrated composites where staple fibers of polypropylene, polyester, cotton and other materials are integrated into an elastomeric meltblown web. Certain elastomeric single-site or metallocene-catalyzed olefin polymers and copolymers are also suitable for the side panels. As shown in FIG. 2, the stretchable side panels are preferably rectangular in shape, and preferably extend from the top of the waist opening 10 to the leg openings 12 and 14. The side panels may also be laminates of multiple layers, and are preferably breathable to water vapor but impervious to liquids.

The waste containment section 4 includes a substantially liquid-impermeable outer cover layer 16, an absorbent layer 17, a liquid-permeable surge layer 13, and a liquid-permeable body side liner 21. These layers are constructed of conventional materials, and are bound together using conventional adhesives, as described below. In accordance with the invention, the outer cover layer 16 is much wider than the absorbent layer 17, especially in the central portion 15 of the absorbent garment between the leg openings 12 and 14.

The portions 54 of the outer cover 16 which extend beyond the absorbent layer 17 serve as seamless leak guards. By "seamless", it is meant that the leak guards are not separately attached and, thus, do not require a seam for attachment to the waste containment section 4. To effectively serve as leak guards, the difference in width between the absorbent layer and outer cover (between folded edges 55 and 57 in FIG. 3) must be substantial, as opposed to trivial, in the central region 15 between the leg openings. Generally, the outer cover 16 is at least about 40% wider than the absorbent layer 17 in the central region 15. Preferably, the outer cover 16 is at least about 60% wider than the absorbent layer 17 in the central region 15. More preferably, outer cover 16 is at least about 80% wider, and most preferably at least about 100% wider than absorbent layer 17 in central region 15 on the underside of the garment.

The seamless leak guards may also be defined with reference to FIGS. 2–3, in terms of the shortest distance "d" between the first and second leg openings measured along a line which follows the outer contour of central region 15 of waste containment section 4. The leak guards should constitute at least about 25% of this distance, preferably at least about 35% of this distance, more preferably at least about 45%, most preferably at least about 50%.

In the embodiment shown in FIG. 3, the outer cover 16 is about 100% wider than the absorbent layer 17 in the central region. Furthermore, the outer cover 16 is configured as a perfect rectangle from the front to the back of the garment, and through the central region. The rectangular configuration of outer cover 16 facilitates ease of manufacture of the outer cover, ease of attachment of adhesives and elastic straps to the outer cover, and provides for large and effective leak guards on both sides of the absorbent layer in the central region.

Elastic bands 19 are mounted to the outer cover layer 16 as shown, for instance, in FIG. 3. The elastic bands 19 preferably extend through the central region 15, and substantially parallel to edges 55 and 57 of the outer cover 16. The elastic bands 19 run adjacent to the narrowest portion of the absorbent layer 17, in the central region 15 defining the leg openings. The elastic bands 19 may be attached to the outer cover 16 by a variety of techniques including adhesive bonding, ultrasonic bonding, thermal bonding, stitch bonding or the like. There are preferably at least two elastic bands 19, more preferably at least four elastic bands 19, adjacent both sides of the absorbent core 17.

In a preferred embodiment, the elastic bands 19 are attached to outer cover 16 inward from the fold edges 55 and 57, with the outer cover being folded over to envelop and encapsulate the elastic bands 19. Again, the folding over of the edges may occur in either direction, namely toward or away from the body-facing side of the outer cover 16. Referring to FIGS. 2–3, outer cover 16 (which includes two layers 35 and 37 joined by adhesive 39, as explained below) is folded over along fold edge 55 so that an inner edge 61 is located substantially inward from folded edge 55. Elastic bands 19 are sandwiched between the layers 35 and 37 in the folded-over portion, and near the inner edge 61 of outer cover 16. Outer cover 16 is also folded along fold edge 57 so that inner edge 63 is substantially inward from folded edge 57. Elastic bands 19 are sandwiched between layers 35 and 37 in this second folded over region, and near the inner edge 63 of outer cover 16.

The material used for the elastic bands 19 may be conventional, as described below. However, in order for the elastic bands 19 to optimize the performance of leak guards defined by outer cover extensions 54, it is important that the elastic bands pull the edges 55 and 57 mostly upward and toward the wearer. This upward pulling of the edges 55 and 57 of the leak guards, toward the wearer, is best accomplished when the outer cover layer 16 is substantially rectangular, as shown in FIG. 3. When the elastic bands 19 are placed inward from the edges 55 and 57 of a rectangular outer cover, the bands 19 are oriented substantially in the direction of the desired pulling force (i.e., upward in both the front and back of the garment). If the elastic bands 19 were instead mounted to curve inward in the central crotch region then the vectoral component of the pulling force during wear, which pulls the edges 55 and 57 upward, would be less pronounced. Depending on the size of the wearer and the size of the garment 2, the elastic bands 19 will also, to a degree, pull the edges 55 and 57 inward against the wearer's skin.

The elastic bands 19 may be in the form of single or multiple bands per leg. A wide variety of elastic materials may be employed. Examples include a film or meltblown web formed using block or graft copolymers of butadiene, isoprene, styrene, ethylene-methyl acrylate, ethylene-vinyl acetate, ethylene-ethyl acrylate or blends thereof. One preferred elastomeric is a block copolymer of styrene-ethylbutadiene-styrene. Specific materials of which elastic bands 19 can be made are the Kraton G series from Shell Chemical Company, such as Kraton G-1650, Kraton G-1652, Kraton GX-1657 and preferably Kraton G-2740X. Also, the Kraton D series can be used, as well as polyester elastomeric materials, polyurethane elastomeric materials and polyamide elastomeric materials. Elastomeric single-site or metallocene-catalyzed olefin polymers and copolymers can also be employed. Also, elastic bands 19 can be made of an activatable material applied in an unstretched condition, and activated by heat, light or moisture or radiation to cause shrinkage and elasticity. Activatable elastic materials can be obtained from the 3M Company.

Each leg elastic band 19 preferably has a width of about 0.05 inch to about 3 inches, more preferably about 0.15 inch to about 1.5 inches, most preferably about 0.25 inch to about 1.0 inch. Each band 19 preferably has elongation of 25–350%, more preferably about 30–260%, most preferably about 25–200%. The length of elastic bands 19 should substantially cover the lengths of the leak guards 54, so that both fastened ends at bands 19 are oriented substantially upward (toward the waist area) on the wearer. If the elastic bands are not long enough that both ends point toward the wearer's waist, then the upward pulling force exerted by the bands on edges 55 and 57 of leak guards 54 will be reduced. Depending on the garment size, bands 19 may have a length of at least about 2 inches, preferably at least about 3 inches, more preferably at least about 4 inches.

Elastic bands 19 can be attached to the outer cover 16 using heat sealing, ultrasonic bonding, adhesive sealing, or other conventional techniques. Suitable adhesives include hot melt adhesives, spray adhesives, self-adhering elastomeric materials and the like. An adhesive layer (not shown) may be positioned between the elastic bands 19 and either layer (35 or 37) of the outer cover 16. Often, the elastic bands will be applied in the stretched condition to the outer cover 16, and then allowed to retract, causing gathering of the outer cover at the edges 55 and 57 when the bands 19 are retracted.

The outer cover 16 may include a single layer, or may include multiple layers joined together. Outer cover 16 shown in FIG. 4 includes two layers 35 and 37, joined by an outer cover adhesive layer 39. Outer cover 16 can be made from a wide variety of woven or nonwoven material, films, or a film-coated nonwoven material, including, for instance, cast or blown films of polyethylene, polypropylene, polyester or blends thereof. Outer cover 16 may also be a composite of a bonded carded or spunbonded or meltblown material, for example, a spunbonded-meltblown composite of thermoplastic material or a spunbonded-meltblown-spunbonded thermoplastic material, wherein the spunbonded layer can provide a cloth-like texture and the meltblown layer can provide liquid impermeability. Materials of which outer cover 16 can be made include nonwovens having a high basis weight, such as about 0.4 ounces per square yard, or greater.

Outer cover 16 can also include extruded films of polyolefin polymers or copolymers, or other thermoplastic materials. Generally outer cover 16 will have a length from about 12 inches to about 30 inches, and a width from about 3 inches to about 20 inches, depending on the wearer's size. In the embodiment shown in FIG. 4, outer cover 16 may include a woven or nonwoven cloth outer layer 35 and liquid-impervious film inner layer 37, joined by adhesive layer 39. Layers 35 and 37 may be joined using the same adhesives, or other bonding techniques, described above for the attachment of elastic bands 19.

The outer cover 16, absorbent layer 17, surge layer 13 and body side liner 21 may also be joined together using ultrasonic bonding, thermal bonding, stitch bonding, or any of the adhesive materials described above. As shown in FIG. 4, the end regions of liner 21 may be tucked between the folded over regions of outer cover 16 and bonded into place using adhesive layer 41. This way, the surge layer and absorbent layer are surrounded by the liner 21 and outer cover 16. Surge layer 13 may be bonded to absorbent layer 17 using adhesive layer 43, and to body side liner 21 using adhesive layer 45. As shown in FIG. 3, the absorbent layer 17, surge layer 13 and body side liner 21 are substantially narrower than outer cover 16 in the central region 15 of the garment 2. The layers 17, 13 and 21 are also somewhat narrower than outer cover 16 in the regions corresponding to the front and back of the garment.

In the vicinity of the waist opening 10, waist elastic regions 22 may be attached to or embedded within the garment. The waist elastic regions 22 may include single or multiple elastic bands constructed from the same materials as leg elastic bands 19. Waist elastic regions 22 in the front and back of the garment preferably have lengths which are nearly the same, or slightly shorter than the width of the outer cover 16. The waist elastic bands may be attached to the outer cover 16 using the same techniques described above for attaching leg elastic bands 19.

Absorbent layer 17 can be made of wood pulp fluff or a mixture of wood pulp fluff and a superabsorbent material, or a wood pulp fluff integrated with a thermoplastic absorbent material treated with a surfactant. Thermal binders, such as Pulpex® can be used in blends or layering with the fluff and superabsorbent. Layer 17 can also be a batt of meltblown synthetic fibers, a bonded carded web of synthetic or natural fibers or blends thereof, a composite of meltblown fibers and the like. The synthetic fibers can be, but are not limited to, polypropylene, polyethylene, polyester and copolymers of these or other polyolefins.

The term "superabsorbent" or "superabsorbent material" refers to a water-swellable, water-insoluble organic or inorganic material capable, under the most favorable conditions, of absorbing at least about 20 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic superabsorbent material polymers include the alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone), poly (vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Both the surge layer 13 and body side liner 21 are constructed from highly liquid pervious materials. These layers function to transfer liquid from the wearer to the absorbent layer 17. Suitable materials include porous woven materials, porous nonwoven materials, and apertured films. Examples include, without limitation, any flexible porous sheets of polyolefin fibers, such as polypropylene, polyethylene or polyester fibers; webs of spunbonded polypropylene, polyethylene or polyester fibers; webs of rayon fibers; bonded carded webs of synthetic or natural fibers or combinations thereof. Either layer may also be an apertured plastic film. The various layers of garment 2 have dimensions which vary depending on the size and shape of the wearer.

The resulting product is an absorbent garment having seamless leak guards. The seamless leak guards not only reduce manufacturing costs, but also provide better leakage protection than prior art flaps joined to the garment with seams. The absorbent garment can be sized and tailored for a wide variety of uses including, for example, diapers, training pants, swimwear, adult incontinence garments, and the like.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. An absorbent garment, comprising:

a waste containment section having front and rear portions, and a central region;

first and second side panels, each joined to the front and rear portions of the waste containment section;

the waste containment section and side panels defining a waist opening and first and second leg openings; and seamless leak guards forming part of the waste containment section and partially surrounding both leg openings;

wherein the waste containment section includes an absorbent layer having outer edges in the central region, a substantially liquid-impermeable outer cover wider than the absorbent layer and having outer edges adjacent to the leg openings, and elastic bands laterally outward from the absorbent layer in the central region, and closer to the outer edges of the absorbent layer than to the outer edges of the outer cover throughout the central region; and the seamless leak guards being formed from portions of the outer cover which extend beyond the absorbent layer.

2. The absorbent garment of claim 1, wherein the seamless leak guards constitute at least about 35% of a distance defined by a shortest line which joins the first and second leg openings through an outer contour of the central region.

3. The absorbent garment of claim 2, wherein the seamless leak guards constitute at least about 45% of said distance.

4. The absorbent garment of claim 2, wherein the seamless leak guards constitute at least about 50% of said distance.

5. The absorbent garment of claim 1 further comprising the elastic bands substantially aligned with edges of the absorbent layer at the first and second leg openings.

6. The absorbent garment of claim 1, wherein the waste containment section further comprises a liquid-permeable body side liner.

7. The absorbent garment of claim 6, wherein the waste containment section further comprises a surge layer between the body side liner and the absorbent layer.

8. The absorbent garment of claim 1, wherein the outer cover comprises a plurality of layers, at least one of which is substantially liquid-impermeable.

9. The absorbent garment according to claim 8, further comprising: the outer cover comprises two layers and the elastic bands are sandwiched between the two layers.

10. The absorbent garment of claim 1, wherein the seamless leak guards constitute at least about 25% of a distance defined by a shortest line which joins the first and second leg openings through an outer contour of the central region.

11. The absorbent garment of claim 1, wherein the elastic bands are joined to a surface of the outer cover which is folded over to conceal the elastic bands.

12. The absorbent article of claim 1, wherein the first and second side panels comprise an elastic material.

13. The absorbent garment of claim 1, wherein the waste containment section further comprises elastic bands near the waist opening.

14. The absorbent garment of claim 1, wherein each side panel comprises a plurality of adjacent panels.

15. The absorbent garment of claim 1, comprising a diaper.

16. The absorbent garment of claim 1, comprising swimwear.

17. The absorbent garment of claim 1, comprising child training pants.

18. The absorbent article of claim 1, comprising an adult incontinence garment.

19. The absorbent garment according to claim 1, further comprising: the elastic bands being initially on a surface of the outer cover distal to a center of the garment, and the outer cover being secondarily folded to produce a folded portion thereby having an inner edge proximal to a center of the garment and an outer edge distal to a center of the garment, the inner edge of the fold being inward of the outer edge and placing the elastic bands adjacent the absorbent core.

20. The absorbent garment according to claim 19, further comprising: the elastic bands being parallel a longitudinal midline of the absorbent garment.

21. The absorbent garment according to claim 19, further comprising: the outer cover being in a rectangular shape after the secondary folding.

* * * * *